United States Patent [19]

Torii et al.

[11] 4,392,923
[45] Jul. 12, 1983

[54] PROCESS FOR PREPARING THIAZOLINOZETIDINONE DERIVATIVES

[75] Inventors: Sigeru Torii, Akaiwa; Hideo Tanaka, Okayama; Junzo Nokami, Okayama; Michio Sasaoka, Okayama; Norio Saito, Itano; Takashi Shiroi, Okayama, all of Japan

[73] Assignee: Otsuka Kagaku Yakuhin Kabushiki Kaisha, Japan

[21] Appl. No.: 406,505

[22] Filed: Aug. 9, 1982

[51] Int. Cl.$^3$ .......................... C25C 1/00; C07D 99/10
[52] U.S. Cl. ................................ 204/59 R; 260/245.4
[58] Field of Search .................... 204/59 R; 260/245.4

[56] References Cited

U.S. PATENT DOCUMENTS

| | | | |
|---|---|---|---|
| 3,505,187 | 4/1970 | Austin | 204/59 R |
| 3,681,380 | 8/1972 | Cooper et al. | 260/245.4 |
| 4,042,472 | 8/1977 | Hall | 204/59 R |
| 4,091,026 | 5/1978 | Micctich et al. | 260/245.4 |

*Primary Examiner*—John F. Niebling
*Attorney, Agent, or Firm*—Larson and Taylor

[57] ABSTRACT

This invention provides a process for preparing a thiazolinoazetidinone derivative represented by the formula

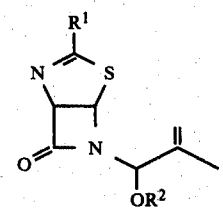

wherein $R^1$ represents aralkyl group or aryloxymethyl group and $R^2$ represents acyl group, the process comprising electrolyzing a compound of the formula

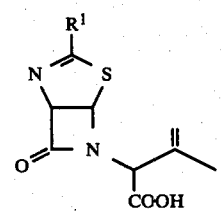

wherein $R^1$ is as defined above in the presence of a lower fatty acid.

11 Claims, No Drawings

PROCESS FOR PREPARING THIAZOLINOZETIDINONE DERIVATIVES

This invention relates to a novel process for preparing thiazolinoazetidinone derivatives and particularly to a novel process for preparing thiazolinoazetidinone derivatives represented by the formula

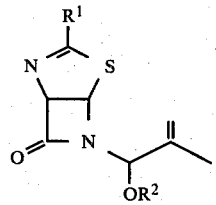
(I)

wherein $R^1$ represents substituted or unsubstituted aralkyl group or substituted or unsubstituted aryloxymethyl group and $R^2$ represents acyl group.

Examples of the substituted or unsubstituted aralkyl groups represented by $R^1$ are benzyl, p-methylphenylmethyl, p-nitrophenylmethyl, 2-phenylethyl and like lower alkyl groups replaced by aryl group optionally substituted with lower alkyl, nitro or like group on the benzene ring. Examples of the substituted or unsubstituted aryloxymethyl groups represented by $R^1$ are phenoxymethyl, p-nitrophenyloxymethyl, p-hydroxyphenyloxymethyl and like methyl groups replaced by aryloxy group optionally substituted with nitro, hydroxy or like group on the benzene ring. Examples of the acyl groups represented by $R^2$ are formyl, acetyl, propionyl, butyryl, isobutyryl, valeryl and like acyl groups having 1 to 6 carbon atoms.

The thiazolinoazetidinone derivatives of the formula (I) are useful as the intermediates for synthesizing penicillin-type and cephalosporin-type antibiotics. For example, according to the process schematically illustrated below, the compound of the formula (I) can be made into a cephalosporin-type compound of the formula (II) useful as an antibacterial agent.

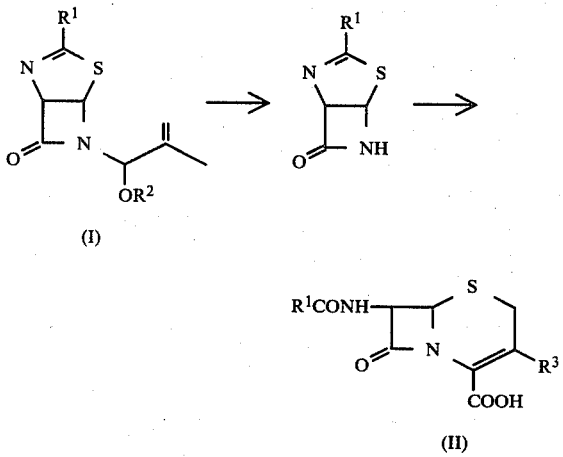

In the foregoing reaction equation, $R^1$ and $R^2$ are as defined above, and $R^3$ represents hydrogen atom, halogen atom or hydroxyl group.

Heretofore processes for preparing thiazolinoazetidinone derivative of the formula (I) are known for example as disclosed in Japanese Unexamined Patent Publication No. 17791/1972. The disclosed process comprises reacting lead tetraacetate with a compound of the formula

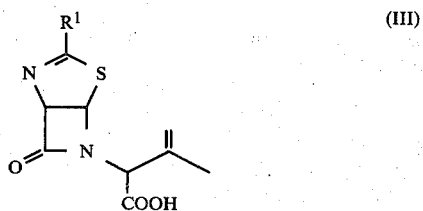
(III)

wherein $R^1$ is as defined above. However, this known process requires highly toxic lead tetraacetate in excess of equimolecular amount relative to the compound of the formula (III), consequently entailing problems of waste disposal, hence uneconomical. For this reason the process is commercially unfavorable.

It is an object of this invention to provide a process for preparing thiazolinoazetidinone derivatives of the formula (I) in a commercially favorable manner.

It is another object of this invention to provide a process for preparing the derivatives in high yields by simplified procedure under mild conditions without using any special reagent.

It is a further object of the invention to provide a process for preparing the derivatives which facilitates the separation and purification of the end product and which is free from the problems arising from the disposal of by-products and the like.

These objects and other advantages will become apparent from the following description.

This invention provides a process for preparing the thiazolinoazetidinone derivative of the formula (I), the process comprising electrolyzing the compound of the formula (III) in the presence of a lower fatty acid.

Examples of the lower fatty acids useful in the process of this invention are formic acid, acetic acid, propionic acid, butyric acid, isobutyric acid, valeric acid and like lower fatty acids having 1 to 6 carbon atoms. Among these acids the acetic acid is preferably used. With this invention, usually such lower fatty acids are usable also as a solvent for the reaction. For this reason, the lower fatty acid is generally used in large excess relative to the compound of the formula (III) serving as the starting material. It is possible to employ a mixture of the fatty acid and other organic solvent as a solvent. Useful organic solvents include tertiary butanol, tertiary amyl alcohol and like tertiary alcohols; methyl acetate, ethyl acetate, methyl propionate and like esters; acetonitrile, butyronitrile, and like nitriles; diethyl ether, dibutyl ether, tetrahydrofuran, dioxane and like ethers; dimethylformamide, diethylformamide and like amides; dichloromethane, dichloroethane, chloroform, carbon tetrachloride and like hydrocarbon halides or mixture thereof.

The electrolysis of this invention is carried out by electrolyzing the starting compound in the presence of a lower fatty acid under electrolytic conditions which are usually employed. The electrolysis can be performed at either controlled potential or constant current. The current density involved is in the range of usually about 1 to about 500 mA/cm$^2$, preferably about 5 to about 100 mA/cm$^2$. The required electric charge is usually about 2 to about 70 F/mol although variable depending on the concentration of the substrate, the kind of the solvent, the shape or type of the electrolytic cell, etc. Useful electrodes include those usually used, such as those of platinum, carbon, stainless steel, lead oxide, titanium, nickel, etc. The reaction temperature is not particularly limited as far as it is below a level at which there occurs the decomposition or conversion of the starting material and reaction product. It is usually about −30° C. to about 80° C., preferably about −20° to about 50° C. The electrolytic cell is used with or without a diaphragm. In the electrolysis of this invention, it is preferred to use a supporting electrolyte. Examples of useful supporting electrolytes are alkali metal salts of lower fatty acids such as potassium formate, sodium acetate, potassium acetate, sodium propionate, etc.; ammonium salts of lower fatty acids such as ammonium formate, ammonium acetate, ammonium propionate, etc.; and amine such as trimethylamine, triethylamine, pyridine, diethylamine, lutidine, piperidine, morpholine, 1,8-diazabicyclo-[5.4.0]-undecene-7, etc. The amount of the supporting electrolyte to be used is usually about 0.1 to about 50 w/v % based on the starting compound although nonlimitative and variable over a wide range.

The compound of the formula (I) thus prepared is easily isolated from the reaction mixture and purified by the usual manner, for example by solvent extraction, column chromatography, etc.

This invention will be hereinafter described in detail with reference to examples given below.

EXAMPLE 1

A 33.6 mg quantity of a compound of the formula (III) (wherein $R^1$ is benzyl) was dissolved in a mixed solvent comprising 2.4 ml of acetic acid and 0.8 ml of tetrahydrofuran. Electrolysis was continued for 96 minutes at a temperature of 4° to 7° C. and a current density of 5 mA/cm$^2$ using carbon electrodes. Thereafter the solvent was removed at reduced pressure and the residue was dissolved in 30 ml of ethyl acetate. The solution was washed with a saturated aqueous solution of sodium hydrogen carbonate. The organic layer was separated, washed with a saturated aqueous solution of sodium chloride, and dried over anhydrous sodium sulfate. The solvent was removed at reduced pressure. The residue was separated and purified by silica gel column chromatography using a 8:1 benzene-ethyl acetate mixture as the developer, giving 26.4 mg of a compound of the formula (I) (wherein $R^1$ was benzyl and $R^2$ was acetyl) in a yield of 86%. To the saturated aqueous layer of sodium hydrogen carbonate was added 5% hydrochloric acid to achieve a pH of 2.0. Then the mixture was extracted with 20 ml of ethyl acetate. The extract was dried over anhydrous sodium sulfate. The solvent was removed at reduced pressure to recover 3.3 mg (10%) of the compound of the formula (III).

The compound of the formula (I) thus prepared was identified by IR and NMR analyses with the following results.

IR(cm$^{-1}$) 1783, 1744, 1615, 1368, 1215, 1025

NMR(CDCl$_3$, δ, ppm) 1.64(b. s, 3H), 1.95, 2.05(2s, 3H), 3.86(s, 2H), 4.97, 5.12(2b. s, 2H), 5.49(d, 1H), 5.88(d, 1H), 6.11, 6.30(2s, 1H), 7.24(b. s, 5H)

EXAMPLES 2 TO 14

The procedure of Example 1 was repeated using compounds of the formula (III) (wherein $R^1$ is benzyl) with the exception of employing the conditions shown in Table 1 given below. Thereby compounds of the formula (I) were produced in the yields indicated in Table 1. The compounds thus prepared were identified by IR and NMR as those of the formula (I) wherein $R^1$ is benzyl and $R^2$ is acetyl. The unreacted materials were recovered in the same manner as in Example 1. The percentages of conversion from the consumed compounds of the formula (III) to the resulting compounds of the formula (I) were more than 95% all in these examples.

TABLE 1

| Ex. | Comp. (mg) [III] | Solvent (ml) | Supporting electrolyte | Current density (mA/cm$^2$) | Electrode | Temperature (°C.) | Time (min.) | Yield (%) |
|---|---|---|---|---|---|---|---|---|
| 2 | 31.1 | AcOH 8 | AcONa 310 mg | 20 | Pt—Pt | 16-25 | 65 | 84 |
| 3 | 32.7 | AcOH 2.4 THF 0.8 | AcONa 60 mg | 10 | c—c | 5-7 | 60 | 80 |
| 4 | 33.4 | AcOH 2.4 THF 0.8 | AcONa 11 mg | 2 | c—c | 2-5 | 170 | 81 |
| 5 | 33.4 | AcOH 2.4 THF 0.8 | AcONa 30 mg | 10 | c—c | 6-10 | 68 | 82 |
| 6 | 30.3 | AcOH 1.5 DME 1.5 | AcONa 60 mg | 5 | c—c | 3-4 | 120 | 91 |
| 7 | 32.8 | AcOH 1.5 DME 1.5 | AcONa 60 mg | 5 | Pt—Cu | 0-2 | 66 | 70 |
| 8 | 41.1 | AcOH 1.5 DME 1.5 | AcONa 65 mg | 5 | C—Cu | 0-2 | 180 | 74 |
| 9 | 33.1 | AcOH 1.5 DME 1.5 | AcONa 60 mg | 5 | Pt—Pt | 1-2 | 118 | 68 |
| 10 | 31.0 | AcOH 1.5 DME 1.5 | Et$_3$N 0.1 ml | 5 | c—c | 0-2 | 126 | 83 |
| 11 | 33.0 | AcOH 1.5 DME 1.5 | Et$_3$N 0.1 ml | 5 | Pt—Pt | 0-2 | 120 | 65 |
| 12 | 32.5 | AcOH 1.5 AcOEt 1.5 | AcONa 60 mg | 50 | c—c | 1-2 | 30 | 64 |
| 13 | 31.8 | AcOH 1.5 AcOEt 1.5 | AcONa 138 mg | 5 | Pt—Pt | 0-1 | 120 | 79 |
| 14 | 32.9 | AcOH 1.5 DME 1.5 | AcONa 60 mg | 5 | c—c | −3 ∼ −2 | 120 | 87 |

We claim:
1. A process for preparing a thiazolinoazetidinone derivative represented by the formula

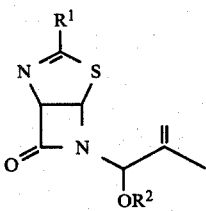

wherein R¹ represents aralkyl group or aryloxymethyl group and R² represents acyl group, the process comprising electrolyzing a compound of the formula

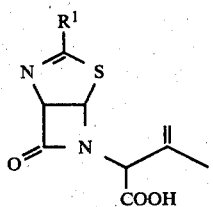

wherein R¹ is as defined above in the presence of a lower fatty acid.

2. A process as defined in claim 1 in which a compound wherein R¹ is benzyl is used.

3. A process as defined in claim 1 in which a thiazolinoazetidinone derivative wherein R¹ is benzyl and R² is acetyl is prepared.

4. A process as defined in claim 1 in which the lower fatty acid is at least one member selected from the group consisting of formic acid, acetic acid, propionic acid, butyric acid, isobutyric acid and valeric acid.

5. A process as defined in claim 1 in which the electrolysis is conducted in a mixture of a lower fatty acid and an organic solvent.

6. A process as defined in claim 5 in which the organic solvent is tetrahydrofuran.

7. A process as defined in claim 1 in which the electrolysis is carried out by using a supporting electrolyte.

8. A process as defined in claim 7 in which the supporting electrolyte is at least one member selected from the group consisting of alkali metal salt of lower fatty acid, ammonium salt of lower fatty acid, amine salt of lower fatty acid and amine.

9. A process as defined in claim 1 in which the electrolysis is effected at a temperature of −30° to 80° C.

10. A process as defined in claim 1 in which the electrolysis is performed at a current density of 1 to 500 mA/cm².

11. A process as defined in claim 1 in which the electrolysis is conducted by passing current with an electric charge of 2 to 70 F/mol through the electrolyte.

* * * * *